US006730043B2

United States Patent
Krueger et al.

(10) Patent No.: US 6,730,043 B2
(45) Date of Patent: May 4, 2004

(54) BONE MARROW BIOPSY NEEDLE

(75) Inventors: John Krueger, Milwaukee, WI (US); Grant A. Clark, Bristol, WI (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/799,143

(22) Filed: Mar. 5, 2001

(65) Prior Publication Data

US 2001/0009978 A1 Jul. 26, 2001

Related U.S. Application Data

(63) Continuation-in-part of application No. 09/552,444, filed on Apr. 18, 2000, now Pat. No. 6,443,910.

(51) Int. Cl.[7] .............................................. A61B 10/00
(52) U.S. Cl. .................................................... 600/567
(58) Field of Search ................................ 600/562, 572; 604/158–169.01, 170.02, 164.02–164.06, 164.11

(56) References Cited

U.S. PATENT DOCUMENTS

| 2,219,605 A | 10/1940 | Turkel |
| 2,827,039 A | 3/1958 | Seiger |
| 3,007,471 A | 11/1961 | McClure, Jr. |
| 3,570,498 A | 3/1971 | Weighton |
| 3,606,878 A | 9/1971 | Kellogg, Jr. |
| 3,844,272 A | 10/1974 | Banko ........................ 128/2 B |
| 3,882,849 A | 5/1975 | Jamshidi ..................... 128/2 B |
| 3,995,619 A | 12/1976 | Glatzer ........................ 128/2 B |
| 4,010,737 A | 3/1977 | Vilaghy et al. .............. 128/2 B |
| 4,013,080 A | 3/1977 | Froning ....................... 128/347 |
| 4,096,860 A | 6/1978 | McLaughlin ............. 128/214.4 |
| 4,356,828 A | 11/1982 | Jamshidi ..................... 128/754 |
| 4,396,021 A | 8/1983 | Baumgartner ............... 128/754 |

(List continued on next page.)

FOREIGN PATENT DOCUMENTS

| SU | 483978 | 9/1975 |
| SU | 567447 | 8/1977 |
| WO | WO 97/32524 | 9/1997 |
| WO | WO 00/10465 | 3/2000 |

OTHER PUBLICATIONS

Product Brochure Entitled: Bone/Bone Marrow Biopsy Set With "Extraction Cannula" from MD Tech. Aug. 98.
Product Brochure Entitled: "Ranfac's Bone Marrow Biopsy Needles" from Ranfac Corporation.
Medical Device Technologies Inc., Bone/Bone Marrow Biopsy Set with Extraction Cannula.

*Primary Examiner*—Eric F. Winakur
*Assistant Examiner*—Nikita R Veniaminov
(74) *Attorney, Agent, or Firm*—Andrew G. Rozycki

(57) ABSTRACT

The present invention provides a bone marrow biopsy device 10 that includes a handle, an outer cannula, a stylet, and an inner member. The outer cannula is secured in the handle. The outer cannula defines a distal tip that is tapered to provide a distal cutting edge. The stylet is designed to be inserted in the outer cannula. The stylet defines a sharp distal tip. The inner member is designed to be inserted in the outer cannula. The inner member defines a cutting finger.

25 Claims, 6 Drawing Sheets

U.S. PATENT DOCUMENTS

| | | | | |
|---|---|---|---|---|
| 4,403,617 A | 9/1983 | Tretinyak | | 128/754 |
| 4,461,305 A | 7/1984 | Cibley | | 128/754 |
| 4,469,109 A | 9/1984 | Mehl | | 128/754 |
| 4,487,209 A | 12/1984 | Mehl | | 128/754 |
| 4,543,966 A | 10/1985 | Islam et al. | | 128/754 |
| 4,619,272 A | 10/1986 | Zambelli | | 128/753 |
| 4,630,616 A | 12/1986 | Tretinyak | | 128/753 |
| 4,643,196 A | 2/1987 | Tanaka et al. | | 128/753 |
| 4,649,918 A | 3/1987 | Pegg et al. | | 128/305 |
| 4,681,123 A | 7/1987 | Valtchev | | 128/753 |
| 4,682,606 A | 7/1987 | DeCaprio | | 128/754 |
| 4,699,154 A | 10/1987 | Lindgren | | 128/754 |
| 4,702,260 A | 10/1987 | Wang | | 128/753 |
| 4,708,147 A | 11/1987 | Haaga | | 128/753 |
| 4,747,414 A | 5/1988 | Brossel | | 128/754 |
| 4,766,907 A | 8/1988 | DeGroot et al. | | 128/754 |
| 4,774,948 A | 10/1988 | Markham | | 128/329 |
| 4,785,826 A | 11/1988 | Ward | | 128/754 |
| 4,790,329 A | 12/1988 | Simon | | 128/749 |
| 4,793,363 A | 12/1988 | Ausherman et al. | | 128/754 |
| 4,799,494 A | 1/1989 | Wang | | 128/753 |
| 4,799,495 A | 1/1989 | Hawkins et al. | | 128/754 |
| 4,817,631 A | 4/1989 | Schnepp-Pesch et al. | | 128/753 |
| 4,838,282 A | 6/1989 | Strasser et al. | | 128/754 |
| D303,009 S | 8/1989 | Strasser et al. | | D24/24 |
| 4,922,602 A | 5/1990 | Mehl | | 29/460 |
| 4,931,059 A | 6/1990 | Markham | | 606/185 |
| 4,953,558 A | 9/1990 | Akerfeldt | | 128/751 |
| 4,958,625 A | 9/1990 | Bates et al. | | 128/751 |
| 4,986,279 A | 1/1991 | O'Neill | | 128/754 |
| 5,012,818 A | 5/1991 | Joishy | | 128/754 |
| 5,027,827 A | 7/1991 | Cody et al. | | 128/753 |
| 5,031,634 A | 7/1991 | Simon | | 128/754 |
| 5,036,860 A | 8/1991 | Leigh et al. | | 128/754 |
| 5,040,542 A | 8/1991 | Gray | | 128/754 |
| 5,080,655 A | 1/1992 | Haaga | | 604/265 |
| 5,127,916 A | 7/1992 | Spencer et al. | | 606/185 |
| 5,172,701 A | 12/1992 | Leigh | | 128/753 |
| 5,172,702 A | 12/1992 | Leigh et al. | | 128/754 |
| 5,195,988 A | 3/1993 | Haaga | | 604/265 |
| 5,224,470 A | 7/1993 | Schnepp-Pesch et al. | | 128/753 |
| 5,257,632 A | 11/1993 | Turkel et al. | | 128/754 |
| 5,279,306 A | 1/1994 | Mehl | | 128/753 |
| 5,284,156 A | 2/1994 | Schramm et al. | | 128/754 |
| 5,318,543 A | * 6/1994 | Ross et al. | | 604/164 |
| 5,333,619 A | 8/1994 | Burgio | | 128/754 |
| 5,341,816 A | 8/1994 | Allen | | 128/754 |
| 5,348,022 A | 9/1994 | Leigh et al. | | 128/753 |
| 5,357,974 A | 10/1994 | Baldridge | | 128/754 |
| 5,368,045 A | 11/1994 | Clement et al. | | 128/754 |
| 5,385,151 A | 1/1995 | Scarfone et al. | | 128/754 |
| 5,394,887 A | 3/1995 | Haaga | | 128/754 |
| 5,429,138 A | 7/1995 | Jamshidi | | 128/753 |
| 5,449,001 A | 9/1995 | Terwilliger | | 128/754 |
| 5,462,062 A | 10/1995 | Rubinstein et al. | | 600/567 |
| 5,476,101 A | 12/1995 | Schramm et al. | | 128/754 |
| 5,476,102 A | 12/1995 | Como et al. | | 128/754 |
| 5,477,862 A | 12/1995 | Haaga | | 128/754 |
| 5,507,298 A | 4/1996 | Schramm et al. | | 128/754 |
| 5,522,398 A | 6/1996 | Goldenberg et al. | | 600/567 |
| 5,526,821 A | 6/1996 | Jamshidi | | 128/753 |
| 5,595,186 A | 1/1997 | Rubinstein et al. | | 600/567 |
| 5,615,690 A | 4/1997 | Giurtino et al. | | 128/754 |
| 5,634,473 A | 6/1997 | Goldenberg et al. | | 600/567 |
| 5,713,368 A | 2/1998 | Leigh | | 128/753 |
| 5,718,237 A | 2/1998 | Haaga | | 128/751 |
| 5,807,277 A | 9/1998 | Swaim | | 600/567 |
| 5,823,970 A | 10/1998 | Terwilliger | | 600/564 |
| 5,833,628 A | 11/1998 | Yuan et al. | | 600/567 |
| 5,843,001 A | 12/1998 | Goldenberg | | 600/567 |
| 5,868,684 A | 2/1999 | Akerfeldt et al. | | 600/564 |
| 5,885,226 A | 3/1999 | Rubinstein et al. | | 600/564 |
| 5,910,121 A | * 6/1999 | Paolo et al. | | 600/562 |
| 6,007,496 A | 12/1999 | Brannon | | 600/565 |

* cited by examiner

BONE MARROW BIOPSY NEEDLE

RELATED APPLICATION DATA

This application is a continuation-in-part of U.S. patent application Ser. No. 09/552,444 filed on Apr. 18, 2000 now U.S. Pat. No. 6,443,910 issued on Sep. 3, 2002.

FIELD OF THE INVENTION

The present invention relates to medical instruments utilized in securing marrow tissue samples from bone structures.

BACKGROUND OF THE INVENTION

A biopsy medical instrument is an instrument which is designed to take samples of tissue. Typically, a biopsy device that is utilized to obtain samples from bone consists of a hollow cannula that is surrounding a stylet. The stylet includes a sharp distal tip which extends outwardly from the cannula when the stylet is secured inside the cannula. The combined cannula and stylet is used to penetrate through the outer layer of the bone, called the cortex, which is considerably harder than the trabecular bone layer and the tissue within the bone that is sampled, referred to as the marrow. Once the stylet is removed and the cannula is extended further into the medular cavity, thereby capturing marrow tissue for a sample.

The architecture of the tissue sample that is removed by the biopsy device is critical in several respects. Initially, the size of the sample is important, with larger tissue sample sizes representing better samples for subsequent testing to be performed on the tissue. However, the larger the cannula and stylet that are inserted into the bone, the more pain is generated at the site of the penetration for the patient. In addition, it is important that the sample be taken without damaging the marrow tissue. However, in removing the tissue sample the tissue must be excised from the remaining tissue. This removal can result in compromising the tissue sample by damaging the tissue sample.

Several approaches have been taken to secure large, undamaged tissue samples using bone marrow biopsy devices. However, each of these approaches has significant drawbacks which limit commercial and clinical usefulness. For example, one such approach utilized suction provided at the proximal end of the cannula. The suction is designed to pull the tissue sample into the cannula and retain the tissue sample inside the cannula. While in theory such suction would help secure larger tissue samples, in practice exposure to such suction forces results in damage to the marrow tissue when the sample is removed from the patient.

Another approach utilizes a snare in the form of a coil at the distal end of the cannula. When rotated, the coil decreases in diameter to secure the biopsy tissue sample in the cannula. Examples of such devices are disclosed in Goldenberg et al. U.S. Pat. No. 5,522,398 and Goldenberg et al. U.S. Pat. No. 5,634,473. While again in theory such a device would help secure larger tissue samples, in practice it subjects the tissue sample to compression forces which causes damage to the sample.

Other approaches include the use of inwardly projecting members such as scallops within the cannula. Such devices are disclosed in Rubinstein et al. U.S. Pat. No. 5,462,062 and Rubinstein et al. U.S. Pat. No. 5,885,226. The theory behind such devices is that when the tissue sample is inserted into the cannula, the inward direction of the scallops allows the tissue sample to slide over such projecting members but when the tissue sample is removed from the patient the projecting members latch onto the tissue sample to secure the tissue sample in the cannula. Again, however, this theory fails in practice as it causes trauma to the tissue when the tissue sample is removed from the patient.

Other approaches include providing apertures on the side of the cannula which, in theory, allow tissue to expand into such apertures to help secure the tissue sample in the cannula. Likewise, one approach, such as that disclosed in Goldenberg U.S. Pat. No. 5,843,001, utilizes a screw member in the cannula which is designed to urge the tissue inwardly and retain the in the cannula. Once again, providing a cavity for the tissue sample that is not smooth results in damage to the tissue when the tissue sample is removed from the patient.

Yet another approach at securing the biopsy sample within the cannula involves the use of a pair of coaxial cannulas, such as that disclosed in Rubinstein et al. U.S. Pat. No. 5,595,186. One of the two cannulas includes a curved section that acts as a cam to compress the inner cannula around the tissue sample when the inner cannula is withdrawn from the outer cannula. Once again, in theory this would help to secure the tissue within the cannula, but in practice it subjects the tissue sample to such compression forces that damage to the sample is caused. In addition, the use of dual cannulas acts to either decrease the size of the tissue sample or to increase the size of the biopsy device causing increased pain to the patient. A similar approach disclosed by Swaim U.S. Pat. No. 5,807,277 utilizes an additional coaxial hollow cannula designed to sheer or cut-off the tissue when the two cannulas are rotated relative to each other. However, because such devices require additional hardware in the cannula, either the size of the tissue sample is decreased or the size of the biopsy device is increased.

Mittermeier et al. published International Patent Application No. WO 00/10454 discloses a bone biopsy device comprising an outer cannula and inner cannula, wherein the distal end of the inner cannula contains a resilient deformable wall which constricts during the sampling. One drawback of this design is that the interruptions in the tissue receiving portion of the inner cannula facilitate wall deformation thereof, but also compress the obtained sample while compromising the structural integrity of the receiving portion of the inner cannula in operation.

Difficulty has been encountered in the art in the balancing between the structural properties of bone biopsy devices and desired sampling attributes. The ability for bone biopsy devices to sample in a consistent manner without unnecessary damaging forces exerted upon the sample taken has especially proven challenging. In addition to these problems, accommodating patient comfort by reducing the need for multiple site sampling is another challenge.

There exists a need in the art for bone biopsy devices that have improved operative designs and characteristics. What would be desirable is a bone marrow biopsy device that is able to consistently secure a large tissue sample while avoiding increasing the size of the biopsy device thereby minimizing the pain experienced by the patient during the procedure. Also desirable would be a device that avoids subjecting the tissue sample to undue forces, whether such forces be compression, suction, etc. Reducing trauma to the patient from multiple sampling would also be desirable.

SUMMARY OF THE INVENTION

The present invention is able to secure a large tissue sample while avoiding increasing the size of the biopsy device thereby minimizing the pain experienced by the patient during such procedure. The present invention further avoids subjecting the tissue sample to undue forces, whether such forces be compression, suction, etc., thus reducing damage to the tissue following removal of the sample from the patient. Yet another advantage of the invention is that multiple samples can be obtained from a single penetration episode into the bone, thereby reducing the trauma of the biopsy procedure to the patient and increasing patient comfort.

The present invention provides a bone marrow biopsy device that includes a handle, an outer cannula, a stylet, and an inner member. The outer cannula is secured in the handle. The outer cannula defines a distal tip that is tapered to provide a distal cutting edge. The stylet is designed to be inserted in the outer cannula. The stylet defines a sharp distal tip. The inner member is designed to be inserted in the outer cannula. The inner member defines a cutting finger and has a tip which is beveled. When the inner member and outer cannula are assembled, the distal tip of the cutting finger of the inner member terminates at a position proximal to the distal tip of the outer cannula.

Thus, there is disclosed a bone marrow biopsy device comprising a handle; an outer cannula secured in the handle, the outer cannula defining a distal tip that provides a distal cutting edge; a stylet designed to be inserted in the outer cannula, the stylet defining a sharp distal tip; and an inner member designed to be inserted in the outer cannula, the inner member defining a cutting finger.

Thus, there is further disclosed a member for use with a bone marrow biopsy device comprising a proximal end formed with a hub that secures the member; and a distal end that defines a cutting finger.

In a preferred embodiment, the inner member further comprises markings on the surface of the proximal portion thereof to indicate the length of the sample to be obtained relative to the outer cannula. In another preferred embodiment, the cutting finger has a width designed such that the cutting finger is wide enough to maintain the structural integrity of the cutting finger while being sufficiently narrow to avoid subjecting a tissue sample to compression forces. In one embodiment, the width of the cutting finger is from about 60% to about 75% of the circumference of the inner member. In a further preferred embodiment, the cutting finger of the inner member has a length of up to about 4.0 cm.

There is further disclosed a kit for use in obtaining a bone marrow biopsy comprising a handle having an outer cannula secured therein, the outer cannula defining a distal tip that provides a distal cutting edge; a stylet designed to be inserted in the outer cannula, the stylet defining a sharp distal tip; and an inner member designed to be inserted in the outer cannula, the inner member defining a cutting finger.

There is disclosed a method for sampling bone marrow tissue comprising: inserting a stylet into an outer cannula; penetrating the bone cortex with the stylet and the outer cannula; removing the stylet; further inserting the outer cannula into a medular cavity, thereby trapping bone marrow tissue within the outer cannula; extending an inner member into the outer cannula, the inner cannula defining a cutting finger; rotating the inner member to shear off the specimen with the cutting finger; and removing the specimen from the patient.

DETAILED DESCRIPTION OF THE INVENTION

The term "cutting finger" as used herein is meant to refer to the configuration of the distal portion of the inner member as having an overall open semi-cylindrical "trough-like" configuration with a semi-circular cross-sectional configuration. Additional peripheral openings through the surface of the cutting finger body other than the "trough" are not meant to be included.

Figure 1:
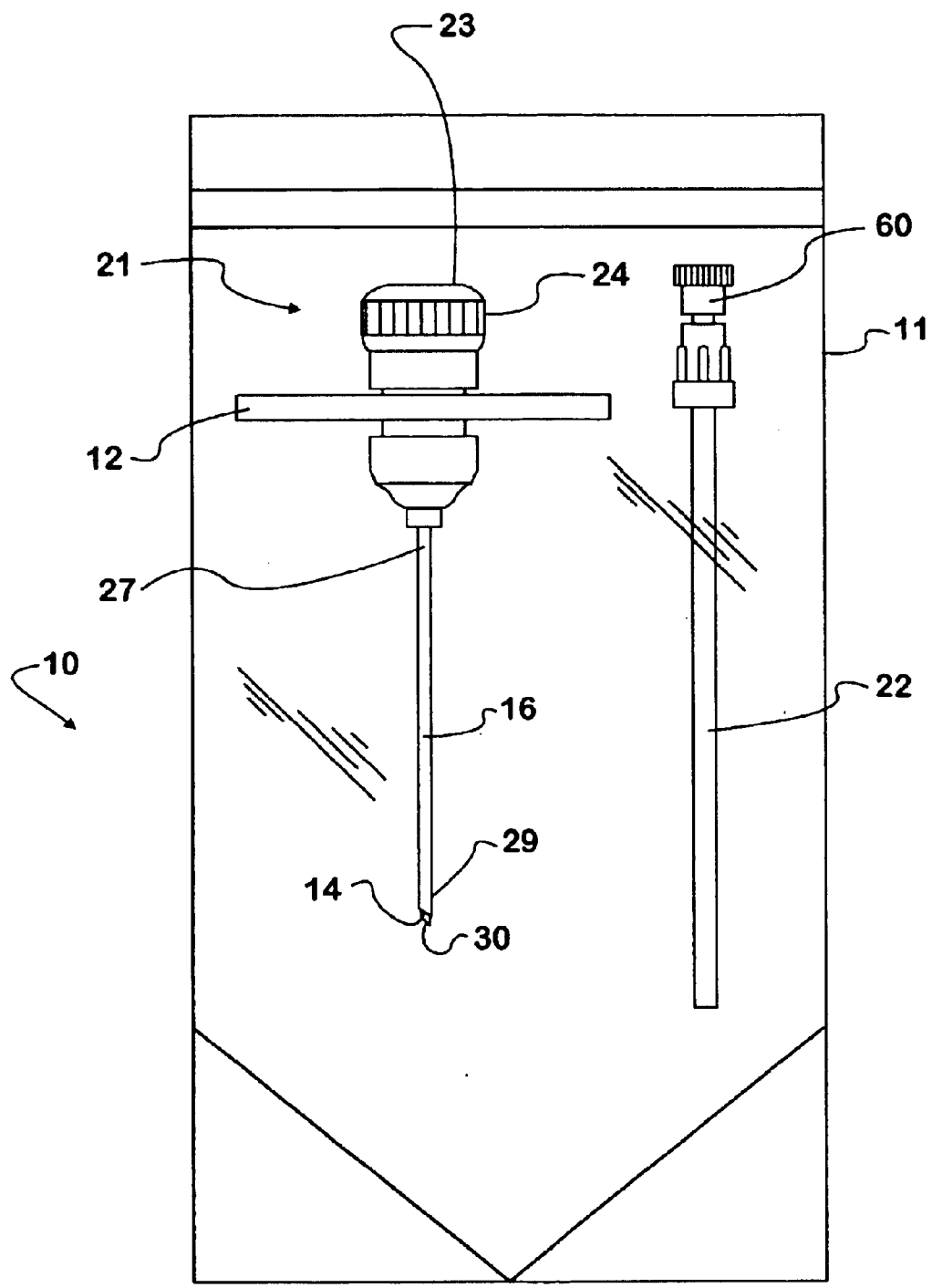
FIG. 1 is an elevational view of an outer cannula and an inner cannula in accordance with the principles of the present invention in the form of a kit packaged in a container.
Figure 2A:
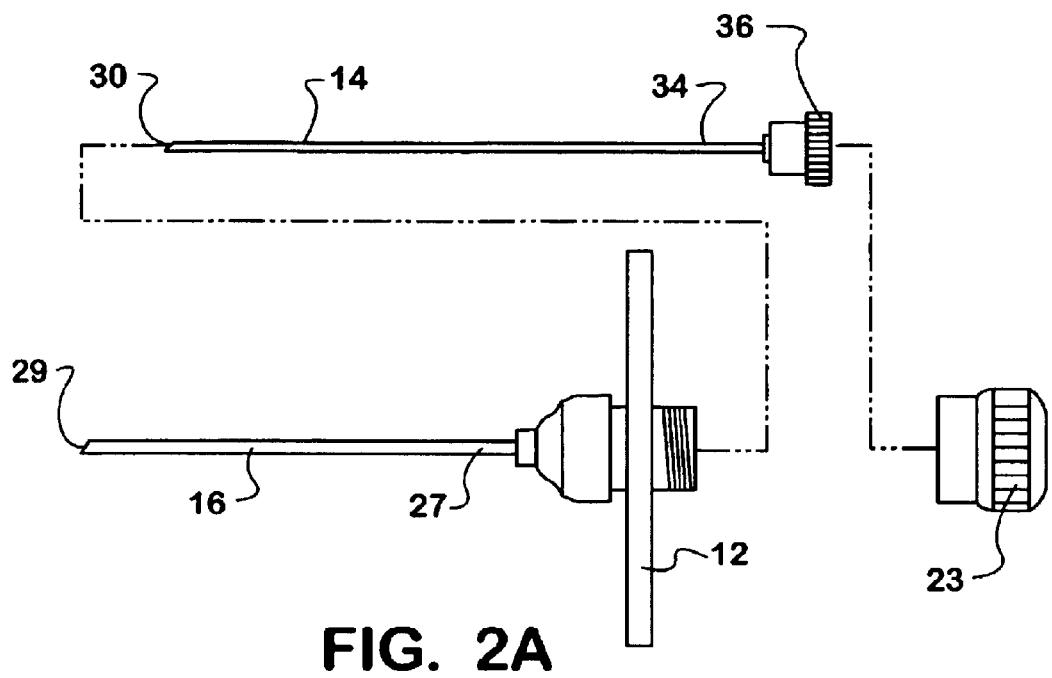
FIG. 2A is a perspective view of the handle including the outer cannula, the cap and the stylet of the bone marrow biopsy device of FIG. 1.
Figure 2B:
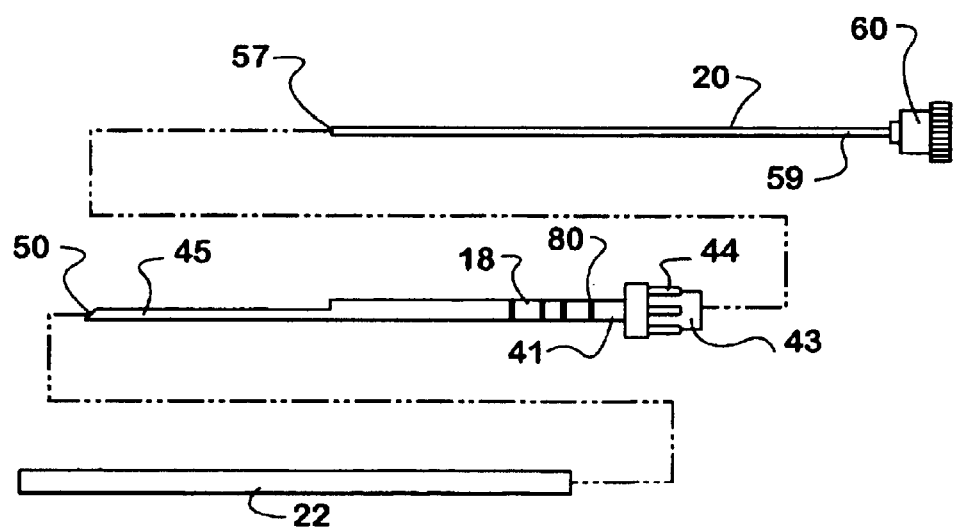
FIG. 2B is a perspective, exploded view of the inner member, the ejector pin, and the protective sheath of the bone marrow biopsy device of FIG. 1.

Referring to FIGS. 1, 2A and 2B, a bone marrow biopsy made in accordance with the principles of the present invention in a package is generally designated by the reference number 10. A bone marrow biopsy device 10 made in accordance with the principles of the present invention includes a handle 12, a stylet 14, an outer cannula 16, an inner member 18, an ejector pin 20, and a protective sheath 22. The bone marrow biopsy device 10 made in accordance with the principles of the present invention is preferably provided to the user sterile in a package 11.

Because the bone marrow biopsy device 10 made in accordance with the principles of the present invention must be inserted through the hard outer cortex layer of a bone, the handle 12 is designed to ergonomically nest in the palm of a health care professional. Thus, a proximal portion 21 of the handle 12 includes a tapered cap 23 designed to fit into the middle portion of the palm. The tapered cap 23 is adapted to engaged to the handle 12. In a preferred embodiment, the tapered cap 23 is threadingly engaged to cooperating threads on the handle 12. In addition, the tapered cap 23 may include a scored outer surface top 24 to assist the health care professional is securing and removing the cap 23.

The handle 12 is designed so that the outer cannula 16 extends between the index and the middle finger of the health care professional. This allows the health care professional to exert a great deal of pressure on the handle 12 from the palm of the hand. This further allows the health care professional to direct the device 10 into the patient utilizing the fingers that are wrapped around the handle 12. In a preferred embodiment, the handle 12 is molded from a hard plastic.

The bone marrow biopsy device 10 made in accordance with the principles of the present invention includes an outer cannula 16. The outer cannula is permanently secured at a proximal end 27 to the handle 12. The distal tip 29 of the outer cannula 16 is tapered to provide a distal cutting edge, best seen in FIG. 2A. The outer cannula is preferably designed of a hard material to withstand the forces applied on the outer cannula 16 when penetrating through the cortex of the bone. Thus, in a preferred embodiment the outer cannula 16 is made of stainless steel.

The bone marrow biopsy device 10 made in accordance with the principles of the present invention also includes a stylet 14, best seen in FIG. 2A. The stylet 14 includes a sharp distal tip 30 designed to penetrate the hard cortex layer of a bone. Like the outer cannula 16, the stylet 14 is preferably designed of a hard material to withstand the forces applied on the stylet 14 when penetrating through the cortex of the bone, such as stainless steel.

A proximal end 34 of the stylet 14 includes a stylet retaining housing 36. The stylet retaining housing 36 is designed to secure the stylet 14 within the handle 12. Thus, the stylet retaining housing 36 is adapted to be contained within the ergonomic design of the cap 23. In addition, the stylet retaining housing 36 is retained within the handle 12 so that the stylet 14 cannot rotate while penetrating the bone cortex. In a preferred embodiment, the stylet retaining housing 36 is relatively square and is secured in a cooperating relatively square receiving cavity (not shown) within the handle 12.

The stylet is adapted to be secured within the outer cannula 16 in order to penetrate the bone cortex. Thus, the outer diameter of the stylet 14 is slightly smaller than the inner diameter of the outer cannula 16. When the stylet 14 is inserted into the outer cannula 16 and the stylet retaining housing 36 is secured in the handle 12, the sharp distal tip 30 of the stylet 14 extends slightly beyond the distal tip 29 of the outer cannula 16, as seen in FIG. 1. Thus, the sharp distal tip 30 of the stylet 14 works in conjunction with the sharp distal tip 29 of the outer cannula 16 to assist in penetrating the bone cortex.

Referring now to FIG. 2B, the bone marrow biopsy device 10 made in accordance with the principles of the present invention also includes an inner member 18. A proximal end 41 of the inner member 18 is formed with a hub 43 that is secured to the inner member 18. The hub 43 includes a plurality of ribs 44 to aid in rotation of the hub 43 during use. In a preferred embodiment and as depicted in FIG. 2B, the surface of inner member 18 at the proximal portion contains markings 80 which indicate the length of the sample to be obtained relative to the outer cannula. Accordingly, this embodiment permits estimation of the sample size without the need for insertion and removal of the ejector pin.

A distal end of the inner member 18 defines a cutting finger 45. The width of the cutting finger 45 is preferably designed such that the cutting finger 45 is wide enough to maintain the structural integrity of the cutting finger while being sufficiently narrow to avoid subjecting the tissue sample to compression forces.

It has been discovered that there exists a relationship between the width of the cutting finger and the overall diameter, or "gauge," of the inner member wherein both the maintenance of the structural integrity of the cutting finger and preservation of the tissue sample can be optimized. In general, as the overall diameter of the inner member increases, a proportionate increase in the width of the cutting finger can be used. Conversely, as a smaller overall diameter of the inner member is used, a smaller width of the cutting finger is preferred. For purposes of the invention, the width of the cutting finger can range from about 60% to about 75% of the circumference of the inner member. For example, an inner member having a diameter of about 0.081 inches can have a cutting finger having a width of about 63% of the circumference of the inner member. In another example, an inner member having a diameter of about 0.119 inches can have a cutting finger having a width of about 74% of the circumference of the inner member.

Figure 3A:
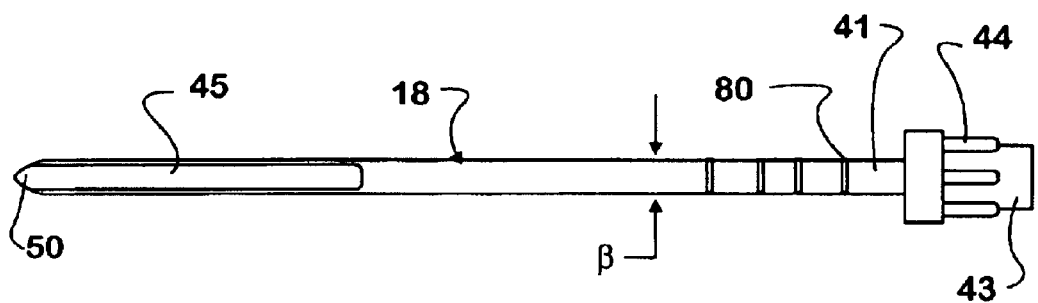
FIG. 3A is a close-up top view of the inner member showing the cutting finger of FIG. 2B.
Figure 3B:
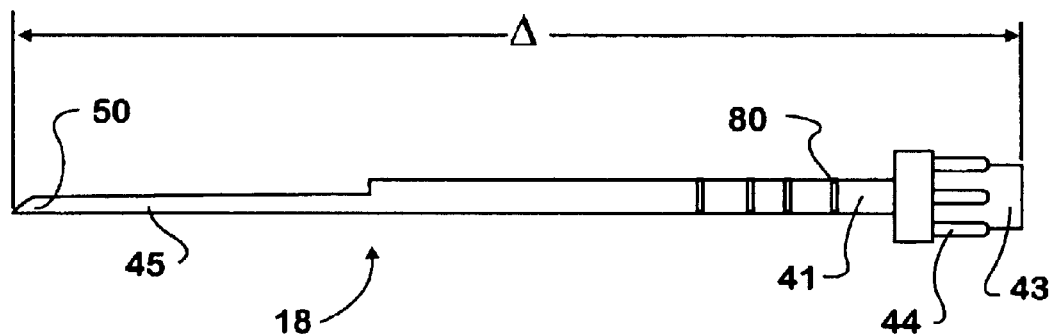
FIG. 3B is a close-up side view of the inner member showing the cutting finger of FIG. 2B.
Figure 4:
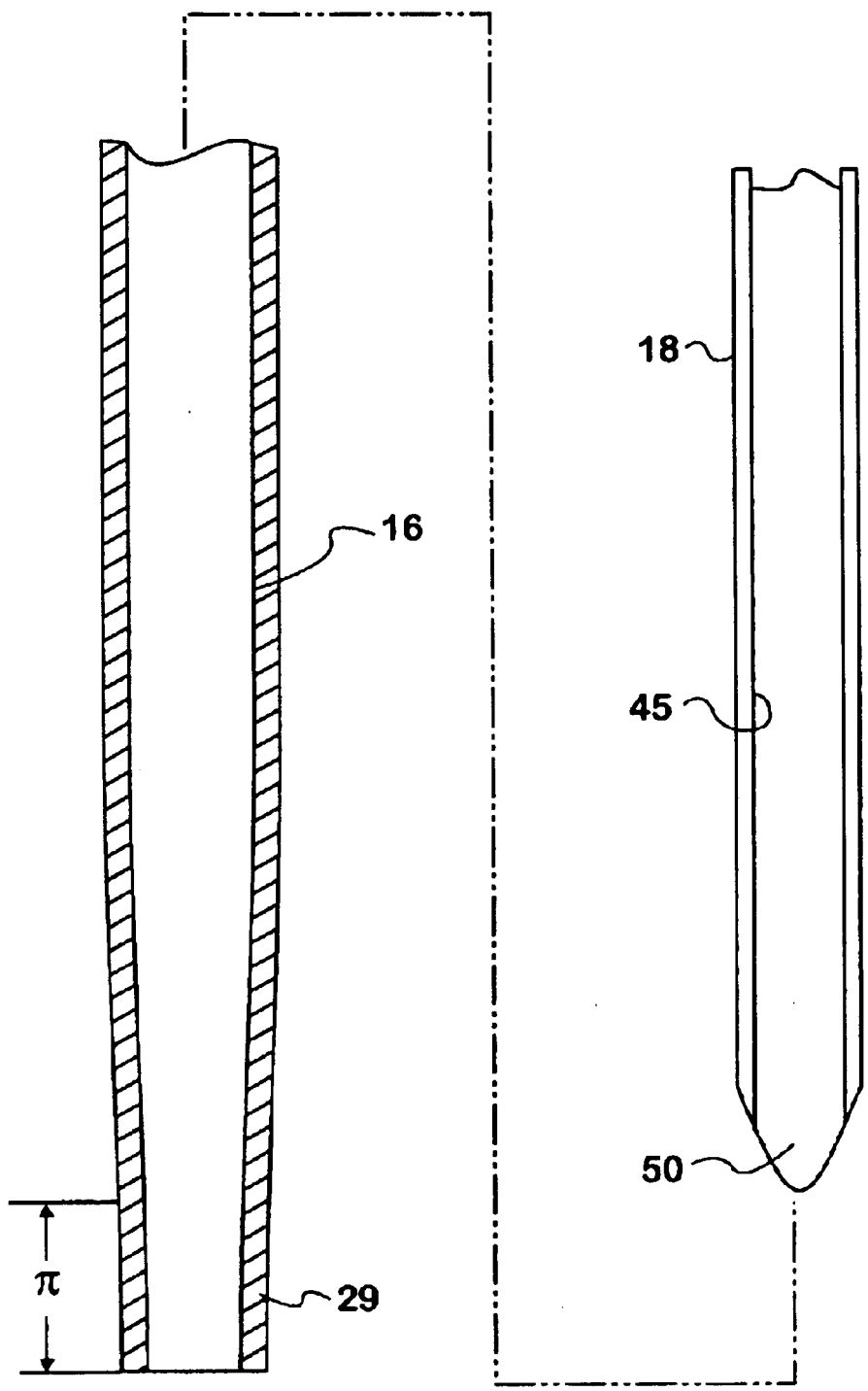
FIG. 4 is a close-up top view of the cutting finger of FIG. 3 and cross-sectional view of the outer cannula of FIG. 2.

Referring now to FIGS. 3A, 3B and 4, close-ups of the cutting finger 45 are seen. By cutting finger 45, it is seen in one embodiment as a blade-type member having generally sharp edges that is capable of cutting the tissue sample substantially from the bone marrow tissue without subjecting the tissue sample to undue compression forces and while being capable of structurally withstanding the force exerted on the blade.

In one embodiment, the cutting finger is formed by grinding an amount of circumference of the inner member 18 away thereby forming a blade-type member having generally sharp edges. In addition, a distal tip 50 of the cutting finger 45 is beveled to both facilitate transitional movement of the sample into the cutting finger, as well as facilitate the cutting or shearing of the tissue sample upon rotational movement of the inner member. The taper of the distal tip 29 (seen in FIG. 2A) of the outer cannula 16 directs the cutting finger 45 inwardly. The inward extension of the cutting finger 45 causes the cutting finger 45 to sever the tissue sample from the tissue.

In a further preferred embodiment of the invention, the cutting finger of the inner member can have a length of up to about 4.0 cm, thereby permitting overall lengthier samples to be obtained. Alternatively, such a cutting finger length also permits multiple sampling at the same site to be taken without necessitating the removal of the outer cannula portion of the device. By obtaining a lengthier sample as such and analyzing the strata revealed in the sample, the practitioner is able to view pathological changes over time which have occurred in the patient.

As seen in FIG. 2B, the bone marrow biopsy device 10 made in accordance with the principles of the present invention further includes an ejector pin 20. The ejector pin 20 is a solid piece designed to fit within the inner diameter of the inner member 18. A distal end 57 of the ejector pin 20 is blunt to avoid damaging the tissue sample when it is removed from the inner member 18. A proximal end 59 of the ejector pin 20 includes an ejector pin housing 60. The ejector pin housing 60 is designed to secure the ejector pin 20 within the inner member 18.

Finally, the bone marrow biopsy device 10 made in accordance with the principles of the present invention includes a protective sheath 22. The protective sheath 22 is designed to surround the inner member to protect the cutting finger 45 prior to use and be removable from the inner member. In a preferred embodiment, the protective sheath 22 can be made from a plastic such as a low density polyethylene.

Figure 5:
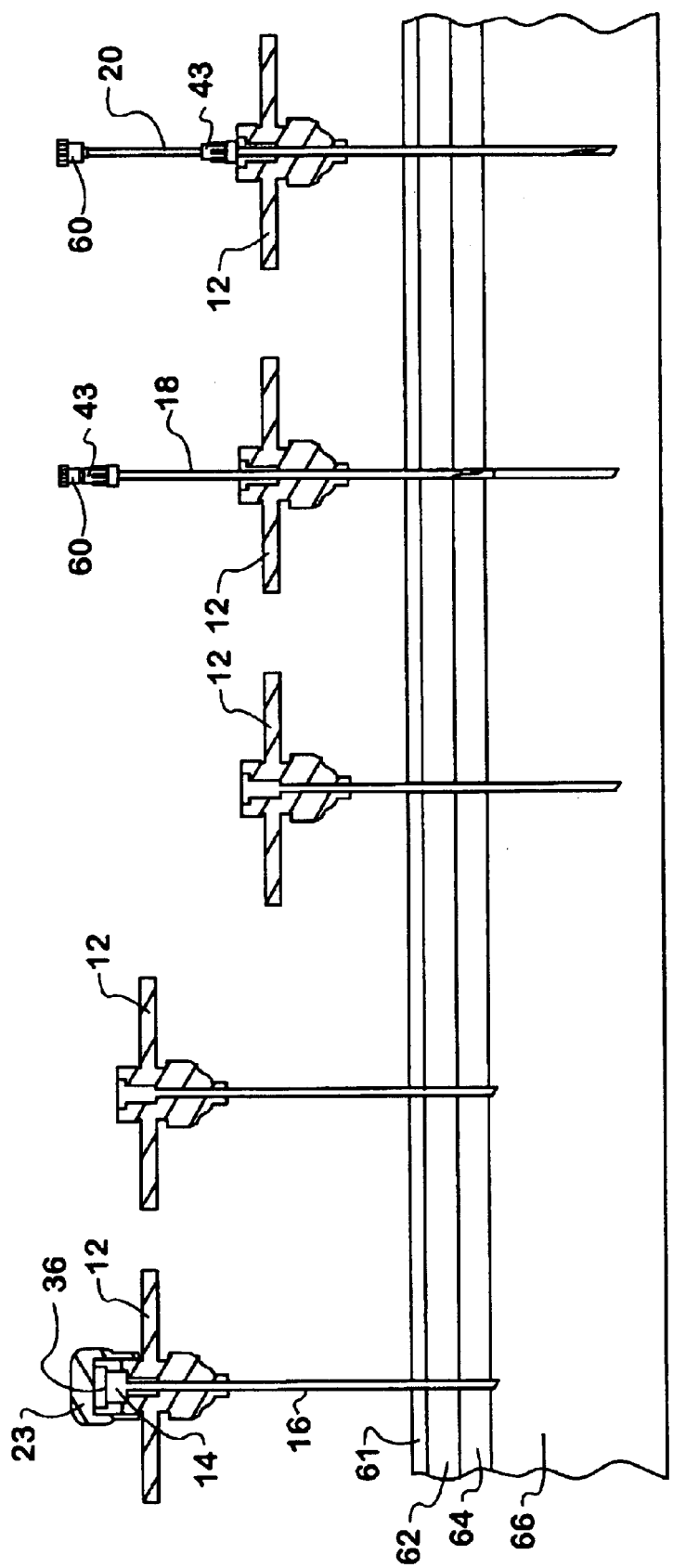
FIG. 5 is a cross-sectional elevational view showing the use of the biopsy device of FIGS. 1 through 3.

Referring now to FIG. 5, use of a bone marrow biopsy device 10 made in accordance with the principles of the present invention is described. The patient comprises outer skin layers 61, a periosteum layer consisting of layers of soft tissue 62, the hard cortex layer of the bone 64, and the medular cavity 66 which contains the bone marrow. In use, the stylet 14 is inserted into the outer cannula 16 and the stylet retaining housing 36 is locked into the handle 12. The health care professional then uses the sharp distal end of the stylet and the beveled distal end of the cannula to penetrate the bone cortex 64. Once the bone cortex 64 has been penetrated and the outer cannula is in the medular cavity 66, the stylet 14 is removed. The outer cannula 16 is then further inserted into the medular cavity 66, thereby trapping bone marrow tissue within the outer cannula 16.

In order to measure the size of the sample, the health care professional can insert the ejector pin 20 into the outer cannula 16. The length of the ejector pin 20 extending outward or proximally from the handle 12 estimates the length of the tissue sample. An alternative and more preferred technique of estimating the size of the sample to be obtained is to view the markings located on the surface of the proximal portion of the inner member, thereby reducing or eliminating altogether the need for insertions and removals of an ejector pin during the sampling stage to estimate sample size.

When an appropriate sample size has been selected, the inner member 18 is extended into the outer cannula 16. The inner member 18 cutting finger 45 slices through a small portion of the tissue sample, with the distal end of the cutting finger 45 extending to within a short distance ($\pi$) (seen in FIG. 4) from the distal end of the outer cannula 16. Accordingly, the difference ($\pi$) in the position of the distal tips of the outer cannula and inner member cutting finger operatively avoids unnecessary compression of the sample. The taper of the distal tip 29 of the outer cannula 16 helps direct the cutting finger 45 inwardly towards the axis of the cannula. The inward extension of the cutting finger 45 helps the cutting finger 45 sever the tissue sample from the tissue.

After the inner member 18 has been fully inserted into the outer cannula 16, the health care professional rotates the inner member 18 by grasping and rotating the hub 43. During this rotation, the cutting finger 45 shears off the specimen while minimizing the amount of crushing effect on the tissue sample. The device of the invention permits 360° rotational movement of the inner member during sampling thereby ensuring complete and clean severance of the sample from the surrounding tissue.

The device 10 can then removed from the patient with the specimen contained within the distal portion of the inner member 18. Alternatively, the device of the invention permits independent operation of the inner member 18 from the outer cannula. One of the advantages of the invention is the ability to sample and remove the inner member without disturbance of the outer cannula, thereby permitting multiple sampling to occur at a single device (outer cannula) penetration location. Accordingly, patient trauma can be significantly avoided by using the device of the invention.

Figure 6A:
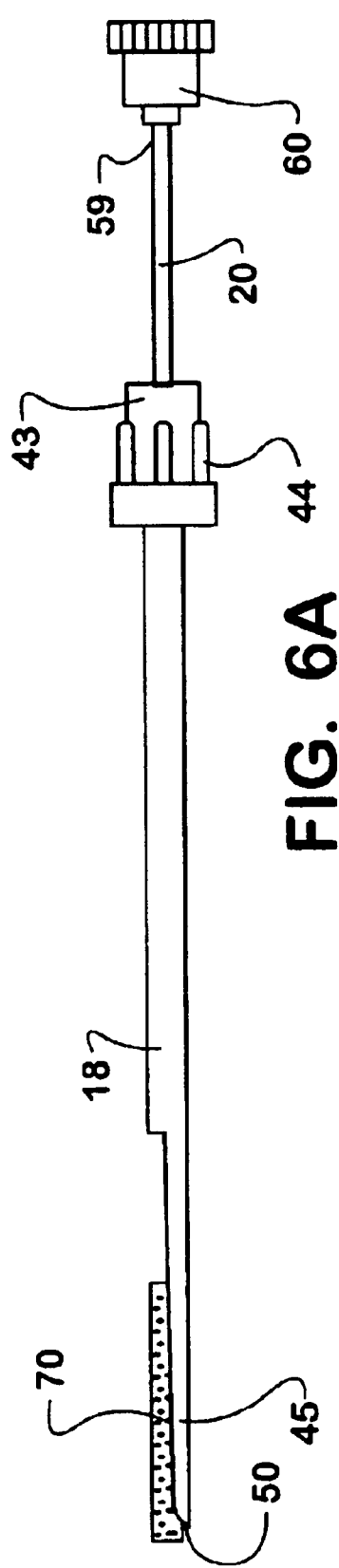
FIG. 6A is a close up view of the inner member and the ejector pin of FIGS. 1 and 2 with the tissue sample in the inner member.
Figure 6B:
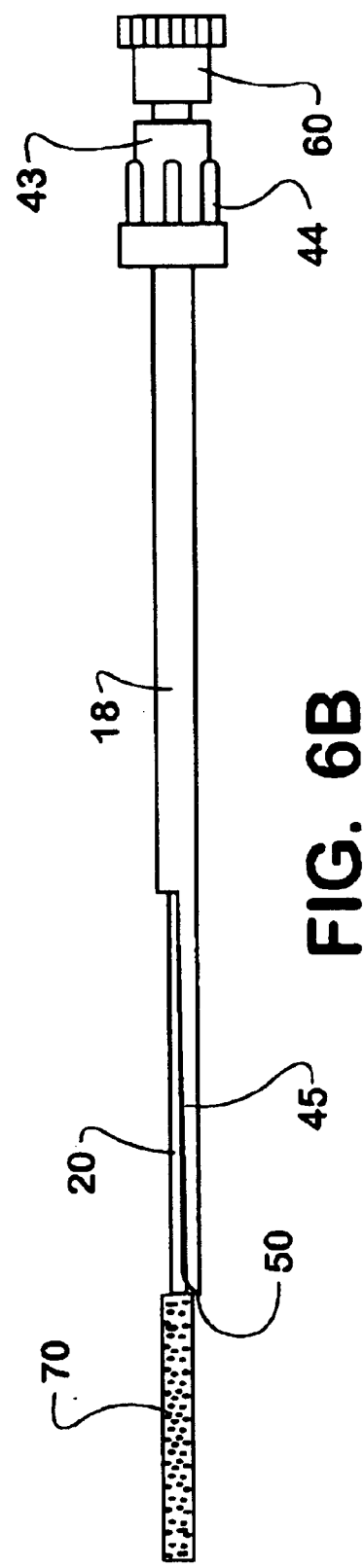
FIG. 6B is a close up view of the inner member and the ejector pin of FIGS. 1 and 2 with the tissue sample removed from the inner member.

Referring now to FIGS. 6A and 6B, the inner member 18, the ejector pin 20, and the tissue sample 70 are seen after removal from the patient. In FIG. 6A the tissue sample 70 remains in the inner member 18. The ejector pin 20 can then be advanced through the inner member 18 to push the specimen out of the inner member 18, as seen in FIG. 6B. Lighter weight ejector pins can be used with relatively heavier inner members in order to reduce the likelihood of damaging or compressing the sample during its removal from the inner member. For example, an 11 gauge ejector pin can be used with an 8 gauge inner member.

The independent operation of the inner member relative to the outer cannula of the device of the invention permits multiple samples to be obtained from a single penetration episode, i.e., a single outer cannula penetration into bone. As a result, the need for multiple site penetration is reduced or eliminated, thereby reducing patient trauma and increasing patient comfort.

Industrial Applicability

Thus, the present invention meets a long-felt need in the medical community that has not been met by others to secure a large tissue sample while avoiding increasing the size of the biopsy device thereby minimizing the pain experienced by the patient during such procedure. The present invention further meets a long-felt need in the medical community that has not been met by others to avoid subjecting the tissue sample to undue forces, whether such forces be compression, suction, etc. The invention also reduces the need for multiple site sampling and further damage to the patient's tissue which accompanies repeated removal and penetration of such devices. The present invention surprisingly provides these and further advantages in a low-cost, easy-to-use device.

It should be understood that various changes and modifications to the preferred embodiment described herein will be apparent to those skilled in the art. Such changes and modifications can be made without departing from the spirit and scope of the present invention and without demising its attendant advantages. It is therefore intended that such changes and modifications be covered by the appended claims.

What is claimed is:

1. A bone marrow biopsy device comprising:
 a handle;
 an outer cannula secured in the handle, the outer cannula defining a distal tip that provides a distal cutting edge;
 a stylet designed to be inserted in the outer cannula, the stylet defining a sharp distal tip; and
 an inner member structured to be inserted in and rotated relative to the outer cannula, the inner member having a proximal tubular portion and a distal portion defining a cutting finger comprising an open, semi-cylindrical structure having a pair of elongate edges and structured to rotatably sever a tissue sample, said inner member further comprising markings on the exterior surface of the proximal portion of said inner member, said markings indicating the length of the sample to be obtained relative to the outer cannula.

2. The bone marrow biopsy device of claim 1 further comprising an ejector pin designed to be inserted into the inner member.

3. The bone marrow biopsy device of claim 1 further comprising a protective sheath designed to surround the inner member.

4. The bone marrow biopsy device of claim 1 wherein the sharp distal tip of the stylet is designed to extend near to the distal tip of the outer cannula.

5. The bone marrow biopsy device of claim 1 wherein the distal tip of the inner member cutting finger is positioned proximal to the distal tip of the outer cannula.

6. The bone marrow biopsy device of claim 1 wherein the cutting finger of the inner member has a length of up to about 4.0 cm.

7. A member for use with a bone marrow biopsy device and structured for insertion through and rotation within relative to an outer cannula, said member comprising:
 a tubular proximal end formed with a hub that secures the member; and
 a distal end defining a cutting finger comprising an open, semi-cylindrical configuration having a pair of substantially parallel elongate edges and beveled distal tip; wherein the cutting finger is structured such that the cutting finger is wide enough to maintain the structural integrity of the cutting finger while being sufficiently narrow to avoid or minimize subjecting a tissue sample to compression forces; and wherein the width of the cutting finger is from about 60% to about 75% of the cross-sectional circumference of the member relative to a complete perimeter circumference thereof.

8. The member of claim 7 wherein the hub includes a plurality of ribs.

9. The member of claim 7 wherein the member includes a proximal portion having markings on the surface.

10. The member of claim 7 wherein the inner member has a diameter of about 0.081 inches and the cutting finger has a width of about 63% of the circumference of the inner member relative to a complete perimeter circumference thereof.

11. The member of claim 7 wherein the inner member has a diameter of about 0.119 inches and the cutting finger has a width of about 74% of the circumference of the inner member relative to a complete perimeter circumference thereof.

12. The member of claim 7 wherein the cutting finger has a length of up to about 4.0 cm.

13. A kit for use in performing a bone marrow biopsy comprising:
  a handle having an outer cannula secured therein, the outer cannula defining a distal tip that provides a distal cutting edge;
  a stylet structured to be inserted in the outer cannula, the stylet defining a sharp distal tip;
  an inner member designed to be inserted in and rotated relative to the outer cannula, the inner member defining a cutting finger comprising an open, semi-cylindrical configuration having a pair of substantially parallel elongate edges and beveled distal tip; wherein the cutting finger is structured such that the cutting finger is wide enough to maintain the structural integrity of the cutting finger while being sufficiently narrow to avoid or minimize subjecting a tissue sample to compression forces; and wherein the width of the cutting finger is from about 60% to about 75% of the cross-sectional circumference of the inner member relative to a complete perimeter circumference thereof.

14. The kit for use in performing a bone marrow biopsy of claim 13 further comprising an ejector pin structured to be inserted into the inner member.

15. The kit for use in performing a bone marrow biopsy of claim further comprising a protective sheath structured to surround the inner member.

16. The kit for use in performing a bone marrow biopsy of claim 13 wherein the cutting finger of the inner member has a length of up to about 4.0 cm.

17. A method for sampling bone marrow tissue comprising:
  inserting a stylet into an outer cannula;
  penetrating the bone cortex with the stylet and outer cannula;
  removing the stylet;
  further inserting the outer cannula into the medular cavity, thereby trapping bone
  marrow tissue within the outer cannula;
  estimating the length of tissue sample by inserting an ejector pin into the outer cannula;
  extending an inner member into the outer cannula, the inner member defining a cutting finger;
  rotating the inner member to shear off the specimen with the cutting finger; and
  removing the specimen from the patient.

18. A bone marrow biopsy device comprising:
  a handle;
  an outer cannula secured in the handle, the outer cannula defining a distal tip that provides a distal cutting edge;
  a stylet structured to be inserted in the outer cannula, the stylet defining a sharp distal tip; and
  an inner member structured to be inserted in and rotated relative to the outer cannula, the inner member defining a cutting finger comprising an open, semi-cylindrical configuration having a pair of substantially parallel elongate edges and beveled distal tip;
  wherein said cutting finger has a width structured such that the cutting finger is wide enough to maintain the structural integrity of the cutting finger while being sufficiently narrow to avoid or minimize subjecting a tissue sample to compression forces; and wherein the width of the cutting finger is from about 60% to about 75% of the cross-sectional circumference of the inner member relative to a complete perimeter circumference thereof.

19. The bone biopsy of claim 18 wherein the inner member has a diameter of about 0.081 inches and the cutting finger has a width of about 63% of the circumference of the inner member relative to a complete perimeter circumference thereof.

20. The bone biopsy device of claim 18 wherein the inner member has a diameter of about 0.119 inches and the cutting finger has a width of about 74% of the circumference of the inner member relative to a complete perimeter circumference thereof.

21. A bone marrow biopsy device comprising:
  a handle;
  an outer cannula secured in the handle, the outer cannula defining a distal tip that provides a distal cutting edge;
  a stylet structured to be inserted in the outer cannula, the stylet defining a sharp distal tip; and
  an inner member structured to be inserted in and rotated relative to the outer cannula, the inner member defining a cutting finger comprising an open, semi-cylindrical configuration having a pair of substantially parallel elongate edges;
  wherein said cubing finger has a width structured such that the cutting finger is wide enough to maintain the structural integrity of the cutting finger while being sufficiently narrow to avoid or minimize subjecting a tissue sample to compression forces; and
  wherein the cutting finger defines a distal tip that is beveled and the distal tip of the outer cannula is tapered such that the taper of the distal tip of the outer cannula directs the cutting finger inwardly when extended near to the distal end of the outer cannula.

22. A method for sampling bone marrow tissue comprising:
  inserting a stylet into an outer cannula;
  penetrating the bone cortex with the stylet and the outer cannula;
  removing the stylet;
  further inserting the outer cannula into the medular cavity, thereby trapping bone
  marrow tissue within the outer cannula;
  estimating the length of tissue sample by viewing markings on the surface of the proximal portion of an inner member relative to the outer cannula;

extending the inner member into the outer cannula, the inner member defining a cutting finger;

rotating the inner member to shear off the specimen with the cubing finger; and removing the specimen from the patient.

23. The method for sampling bone marrow tissue of claim 22 wherein the step of penetrating the bone cortex with the stylet and the outer cannula is achieved by penetrating the bone cortex with a sharp distal end of the stylet and a beveled distal end of the cannula.

24. The method for sampling bone marrow tissue of claim 22 further including the step of extending the distal end of the cutting finger near to the distal end of the outer cannula.

25. The method for sampling bone marrow of claim 22 wherein said rotation of the inner member is about a 360° rotation.

* * * * *